United States Patent
Desi Reddy et al.

(10) Patent No.: US 10,239,910 B2
(45) Date of Patent: Mar. 26, 2019

(54) PROCESS FOR THE PREPARATION OF SOFOSBUVIR

(71) Applicant: OPTIMUS DRUGS (P) LIMITED, Hyderabad (IN)

(72) Inventors: Srinivas Reddy Desi Reddy, Hyderabad (IN); Srinivas Rao Velivela, Hyderabad (IN)

(73) Assignee: OPTIMUS DRUGS (P) LIMITED, Hyderabad (IN)

( * ) Notice: Subject to any disclaimer, the term of this patent is extended or adjusted under 35 U.S.C. 154(b) by 10 days.

(21) Appl. No.: 15/589,691

(22) Filed: May 8, 2017

(65) Prior Publication Data
US 2018/0022774 A1    Jan. 25, 2018

(30) Foreign Application Priority Data
Jul. 20, 2016   (IN) .............................. 201641024792

(51) Int. Cl.
*C07H 19/10*   (2006.01)

(52) U.S. Cl.
CPC .................................... *C07H 19/10* (2013.01)

(58) Field of Classification Search
CPC .................................................... C07H 19/10
See application file for complete search history.

(56) References Cited

U.S. PATENT DOCUMENTS

| | | | | |
|---|---|---|---|---|
| 7,601,820 B2* | 10/2009 | Wang | ................... | C07D 307/33 536/1.11 |
| 7,964,580 B2* | 6/2011 | Sofia | ................... | A61K 31/706 514/43 |
| 8,492,539 B2* | 7/2013 | Chun | ................. | A61K 31/7072 536/1.11 |
| 8,629,263 B2* | 1/2014 | Ross | ..................... | C07H 19/10 536/25.3 |
| 8,859,756 B2* | 10/2014 | Ross | .................... | C07F 7/1856 536/26.1 |
| 2016/0318966 A1* | 11/2016 | Kaushik | ................ | C07H 19/06 |

FOREIGN PATENT DOCUMENTS

| | | |
|---|---|---|
| CN | 103804446 A | 5/2014 |
| WO | WO-2006012440 A2 | 2/2006 |
| WO | WO-2006031725 A2 | 3/2006 |
| WO | WO-2008045419 A1 | 4/2008 |
| WO | WO-2008121634 A2 | 10/2008 |
| WO | WO-2010135569 A1 | 11/2010 |
| WO | WO-2011123645 A2 | 10/2011 |
| WO | WO-201408236 A1 | 1/2014 |
| WO | WO-2014047117 A1 | 3/2014 |
| WO | WO-2014056442 A1 | 4/2014 |

* cited by examiner

*Primary Examiner* — Lawrence E Crane
(74) *Attorney, Agent, or Firm* — Blank Rome LLP

(57) ABSTRACT

The present invention relates to an improved, commercially viable and industrially advantageous process for the preparation of sofosbuvir, which uses reagents that are less expensive and easier to handle.

18 Claims, No Drawings

PROCESS FOR THE PREPARATION OF SOFOSBUVIR

This application claims the benefit of Indian Patent Application No. 201641024792, filed Jul. 20, 2016, which is hereby incorporated by reference.

FIELD OF THE INVENTION

The present invention relates to an improved process for the preparation of sofosbuvir. The present invention involves an environmental friendly process and use of reagents that are less expensive and easier to handle.

BACKGROUND OF THE INVENTION

Sofosbuvir (formerly PSI-7977 or GS-7977) is an approved drug for the treatment of hepatitis C. It was discovered at Pharmasset and then acquired for development by Gilead Sciences. Sofosbuvir is a prodrug that is metabolized to the active antiviral agent 2'-deoxy-2'-a-fluoro-β-C-methyluridine-5'-monophosphate. It is a nucleotide analogue inhibitor of the hepatitis C virus (HCV) polymerase.

Nucleoside phosphoramidate are inhibitors of RNA-dependent, RNA viral replication and are useful as inhibitors of HCV NS5B polymerase, as inhibitors of HCV replication and for treatment of hepatitis C infection in mammals.

Sofosbuvir is chemically known as isopropyl (2S)-2-[[[(2R,3R,4R,5R)-5-(2,4-dioxopyrimidin-1-yl)-4-fluoro-3-hydroxy-4-methyl-tetrahydrofuran-2-yl] methoxy-phenoxy-phosphoryl] amino] propanoate of Formula (I).

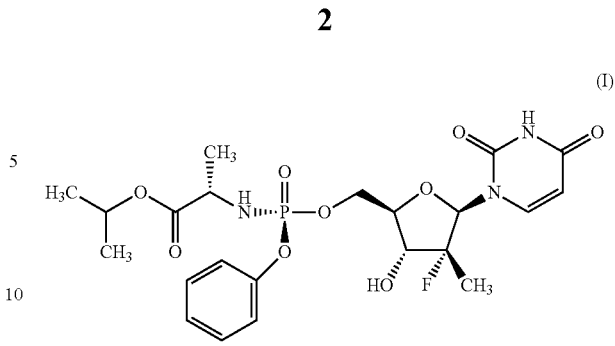

Sofosbuvir was first described in Example 25 of U.S. Pat. No. 7,964,580 B2, which corresponds to WO 2008/121634 A2 and also discloses other novel nucleoside phosphoramidates and their preparations and use as agents for treating viral diseases.

The process disclosed is provided below. The compound of formula VI is protected with a benzoyl group in the presence of benzoyl chloride and pyridine base to obtain the compound of formula V. The amino group of compound V is deprotected in the presence of 80% AcOH under reflux conditions and ammonia/methanol as a solvent was added to get a compound of formula III. The compound of formula III is reacted with a compound of formula IIa to obtain a diastereomeric mixture at "P" of Sp and Rp sofosbuvir. This on chiral resolution by Supercritical Fluid Chromatography (SFC) using 20% MeOH in $CO_2$ as a solvent yields sofosbuvir (I).

The process described herein leads to the production of nucleoside phosphoramidate prodrugs with less than 50% of the desired isomer, which requires additional purifications to get the desired isomer, which enhances the number of steps and cost. This reference does not provide a particular combination of solvents and bases which provides or increases the stereo selectivity during the reaction for the production of the desired Sp isomer.

The above process is schematically shown below.

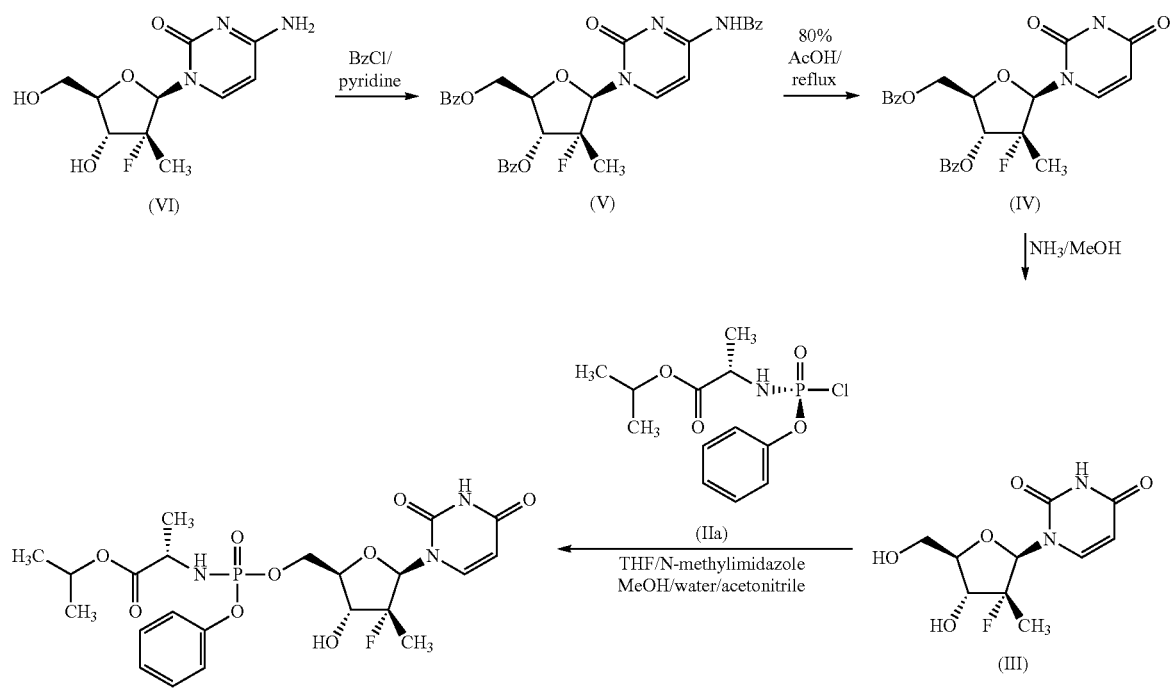

PCT publication no. WO 2011/123645 A2 discloses various crystalline forms and a process for the preparation of (S)-isopropyl 2-(S)-(((2R,3R,4R,5R)-5-(2,4-dioxo-3,4-dihydropyrimidin-1-(2H)-yl)-4-fluoro-3-hydroxy-4-methyl-tetrahydrofuran-2-yl)methoxy)(phenoxy)phosphoryl)-amino)propanoate (sofosbuvir), shown below. A compound of formula (V) is deprotected in the presence of 70% AcOH followed by hydrolysis to obtain a compound of formula III. This is reacted with a compound of formula (II) in the presence of a Grignard reagent to obtain sofosbuvir.

PCT publication no. WO 2014/08236 A1 discloses a process for the preparation of diastereomerically enriched phosphoramidate derivatives. WO 2014/047117 A1, CN103804446A and WO2014/056442 A1 disclose various processes for the preparation of intermediates and nucleoside phosphoramidates compounds.

In view of the foregoing, the present inventors have performed extensive experiments and found that sofosbuvir can be produced in high yield and purity in a simple, efficient, more economical and eco-friendly process.

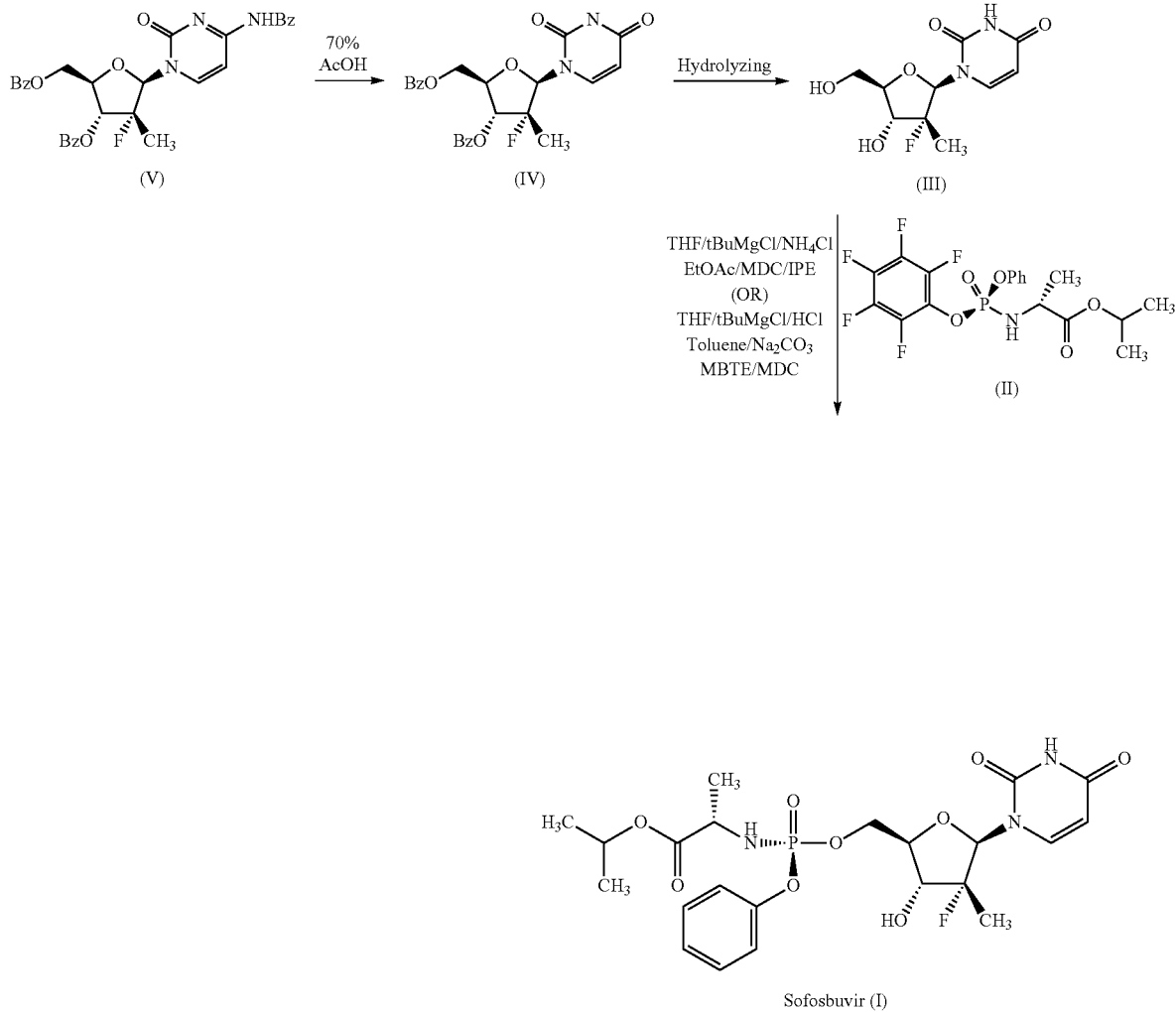

Sofosbuvir (I)

The condensation reaction of the compound of formula (III) with the compound of formula (II) in the presence of a Grignard reagent has low yield and a high impurity profile.

Hence, the use of a Grignard reagent may not be feasible and it is not economical for industrial scale production for the preparation of Sofosbuvir (I).

PCT publication no. WO 2006/012440 A2, WO 2008/045419 A1, WO 2006/031725 A2 and U.S. Pat. Nos. 7,601,820 B2 and 8,492,539 B2 disclose processes for the preparation of intermediates, which can be used for the preparation of sofosbuvir.

PCT publication no. WO 2010/135569 A1 discloses various processes for the preparation of sofosbuvir and its intermediates.

SUMMARY OF THE INVENTION

The present invention relates to an improved, commercially viable and industrially advantageous process for the preparation of sofosbuvir.

One embodiment of the present invention is a process for the preparation of sofosbuvir (I) comprising the step of (a) reacting a compound of formula (III) with a compound of formula (II) in the presence of a metallic salt, a base and a solvent to obtain a compound of formula (I)

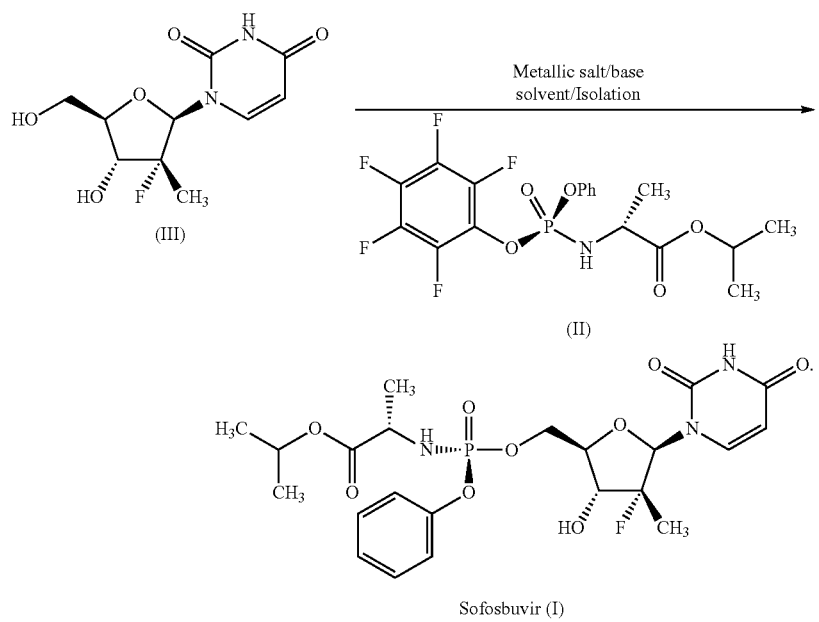

The compound of formula (III) may be prepared by
(i) deprotecting a compound of formula (V), preferably under acidic conditions, to obtain a compound of formula (IV)

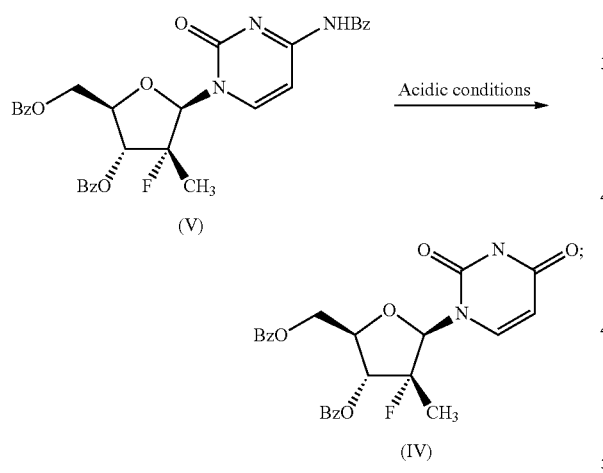

and
(ii) hydrolyzing the compound of formula (IV), preferably in the presence of a base and a solvent, to obtain a compound of formula (III)

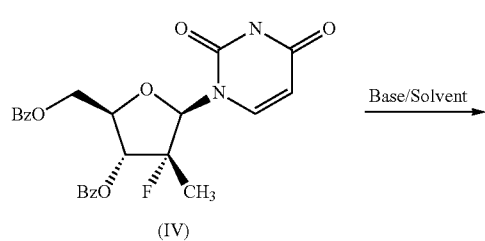

-continued

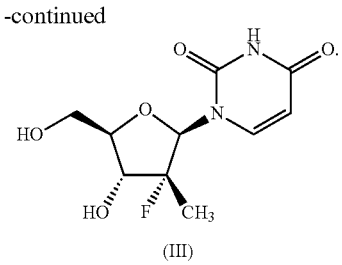

The process of the present invention can be performed without the use of a Grignard reagent and without the use of unsuitable temperatures (such as −20° C. to −15° C.). The process can be performed at room temperature which is advantageous for commercial production.

Yet another embodiment is a composition comprising sofosbuvir and a metallic salt. The metallic salt may be selected from magnesium chloride, magnesium bromide, magnesium iodide, lithium chloride, lithium bromide, lithium iodide, copper chloride, copper bromide, copper iodide, and mixtures thereof. In one embodiment, the metallic salt is magnesium chloride. In another embodiment, the composition comprises sofosbuvir and the metallic salt (such as magnesium chloride) at a weight ratio of at least 98:2, preferably at least 99.5:0.5, at least 99.8:0.2, at least 99.9:0.1, at least 99.95:0.05, or at least 99.98:0.02.

DETAILED DESCRIPTION OF THE INVENTION

The present invention relates to an improved, commercially viable and industrially advantageous process for the preparation of sofosbuvir.

One embodiment is a process for preparing sofosbuvir (I) comprising the step of (a) reacting a compound of formula (III) with a compound of formula (II) in the presence of a metallic salt, a base and a solvent to obtain a compound of formula (I).

Another embodiment is a process preparing sofosbuvir (I) comprising the steps of:
(i) deprotecting a compound of formula (V), preferably under acidic conditions, to obtain a compound of formula (IV);
(ii) hydrolyzing the compound of formula (IV), preferably in the presence of a base and a solvent, to obtain a compound of formula (III); and
(a) reacting a compound of formula (III) with a compound of formula (II) in the presence of a metallic salt, a base and a solvent to obtain a compound of formula (I).

Step (i)

The deprotection of the compound of formula (V) in step (i) may be performed in the presence of a deprotection agent, such as a suitable acid. Suitable acids include, but are not limited to, trifluoroacetic acid, sulphuric acid, methane sulphonic acid, acetic acid, formic acid, hydrochloric acid (including, but not limited to, concentrated hydrochloric acid), and mixtures thereof. A preferred acid is acetic acid (e.g., 80% aqueous acid acid).

In one embodiment, the deprotection of the compound of formula (V) is performed under acidic conditions and under reflux conditions over night till completion of reaction. The reaction mixture can then be cooled to 15° C. and allowed to stir, and then the temperature raised to obtain the compound of formula (IV). The obtained, precipitated compound of formula (IV) can be filtered, washed with solvent and dried to obtain the desired product of formula (IV).

Step (ii)

The hydrolysis step may be performed in the presence of a base and a solvent. The reaction mixture can be allowed to stir at a reduced temperature (e.g., at 0° C. for 30 min), warmed to room temperature slowly and stirred at the same temperature for another 18-24 hours to obtain the compound of formula (III).

Suitable solvents include, but are not limited to, acetone, tetrahydrofuran (THF), acetonitrile, ethyl acetate, dimethylformamide (DMF), dichloromethane, methyl tertiary butyl ether, methanol, ethanol, isopropanol, water and mixtures thereof (such as a mixture of acetonitrile and ethyl acetate). A preferred solvent is methanol.

Suitable bases include, but are not limited to, triethylamine, diisopropylethylamine, diisopropylamine, pyridine, ammonium acetate, ammonium chloride, ammonium formate, ammonium sulfamate, ammonium phosphate, ammonium citrate, ammonium carbamate, ammonia, and mixtures thereof. A preferred base is ammonia. In another embodiment, the base is triethyl amine or diisopropylethylamine.

Step (a)

The compound of formula (III) may be reacted with the compound of formula (II) in the presence of a metallic salt, a base and a solvent. The reaction can be performed at room temperature under nitrogen atmosphere at 25-30° C. and allowed to stir for 2-6 hrs. at the same temperature. The resultant solvent in the reaction mixture can be distilled out at a suitable temperature and the product can be further purified with a suitable solvent (e.g., by recrystallization) to isolate the sofosbuvir of formula (I).

Suitable solvents include, but are not limited to, acetone, tetrahydrofuran, acetonitrile, ethyl acetate, dimethylformamide, dichloromethane, methyl tertiary butyl ether, acetic acid, methanol, ethanol, isopropanol, water and mixtures thereof (such as a mixture of acetonitrile and ethyl acetate). A preferred solvent is tetrahydrofuran.

Suitable bases include, but are not limited to, triethylamine, diisopropylethylamine, diisopropylamine, pyridine, ammonium acetate, ammonium chloride, ammonium formate, ammonium sulfamate, ammonium phosphate, ammonium citrate, ammonium carbamate, ammonia, and mixtures thereof. A preferred base is ammonium chloride (e.g., aqueous ammonium chloride). In another embodiment, the base is triethyl amine or diisopropylethylamine.

Suitable metallic salts include, but are not limited to, magnesium chloride, magnesium bromide, magnesium iodide, lithium chloride, lithium bromide, lithium iodide, copper chloride, copper bromide, copper iodide, and mixtures thereof. A preferred metallic salt is magnesium chloride.

In a preferred embodiment, step (a) is performed in the absence of a Grignard reagent.

The resulting sofosbuvir can be purified by techniques known in the art, such as the use of an anti-solvent, recrystallization, filtration and evaporation. In one embodiment, the sofosbuvir is subjected to recrystallization, for example in the presence of an ether solvent. Suitable ether solvents include, but are not limited to, diethyl ether, diisopropyl ether, MTBE (methyl tertiary butyl ether), and mixtures thereof. A preferred ether solvent is MTBE.

The present inventors have discovered that the condensation reaction of the compound of formula (III) with the compound of formula (II) carried out in the presence of a metallic salt is industrially feasible, eco-friendly and commercially advantageous for preparation of sofosbuvir and its analogues.

The following examples illustrate the present invention, but should not be construed as limiting the scope of the invention.

EXAMPLES

Example-1

Preparation of 3',5'-dibenzoyl-2'-deoxy-2'-fluoro-2'-C-methyluridine $N^4$,3',5'-tribenzoyl-2'-deoxy-2'-fluoro-2'-C-methylcytidine (20 gm) was added to 80% aqueous acetic acid (1 liter) and refluxed overnight till completion of the reaction. After cooling and standing at room temperature (15° C.), most of the product was precipitated and then filtered through a sintered funnel. The resultant precipitate was washed with toluene to give a white solid of the titled product. (Yield: 85-90%).

Example-2

Preparation of 2'-deoxy-2'-fluoro-2'-C-methyluridine

To a solution of 3',5'-dibenzoyl-2'-deoxy-2'-fluoro-2'-C-methyluridine (10 gm) in MeOH (120 mL) was added to a solution of saturated ammonia in MeOH (60 mL). The reaction mixture was stirred at 0° C. for 30 min, warmed to room temperature slowly and then allow to stir for another 18 hours at the same temperature. The solvent in the resultant mixture was evaporated under reduced pressure to give a residue, which was recrystallized with methanol and water to afford the pure product. (Yield: 50-60%).

Example-3

Preparation of (S)-isopropyl-2-(((R)-[(2,3,4,5,6-pentafluoro-phenoxy)-phenoxy-phosphoryl amino] propanoate To a 2 L three-necked round bottom flask fitted with a mechanic stirrer and low temperature thermometer was added 30 g of phenyl dichlorophosphate and 300 mL of anhydrous dichloromethane. The solution was cooled to 0° C. under a nitrogen atmosphere and L-alanine isopropyl ester hydrochloride (23.5 g) was added quickly as a solid. The mixture was stirred and cooled to −55° C. in a dry ice-acetone bath. A solution of 31 g of triethylamine in 150 mL of dichloromethane was added through an addition funnel over 70 minutes. The white cloudy mixture was stirred at −55° C. for half hour and then the temperature was raised to −5° C. slowly over 1.5 h. A pre-cooled mixture of pentafluorophenol and triethylamine in 100 mL of dichloromethane was added to the mixture via an addition funnel over 1 hour at 0° C. and the resulting mixture was stirred at 0° C. for 4 hours. The white precipitate (TEA.HCl) was filtered out and rinsed with dichloromethane. The filtrate was concentrated under reduced pressure and the white solid residue was triturated in 880 mL of t-butyl methyl ether (TBME) at room temperature for one hour. The white suspension was filtered and the solid was rinsed with TBME. The solid was distributed in a mixture of ethyl acetate and water. The organic layer was separated and washed with water. The organic layer was dried over MgSO$_4$ and concentrated to afford a white feather solid. The obtained solid was dissolved in ethyl acetate, washed with water/brine and dried over MgSO$_4$. The resultant solution was concentrated under reduced pressure to obtained title compound. (Yield: 70-80%)

Example-4

Preparation of Sofosbuvir

To a 4 L four-necked round bottom flask fitted with a mechanical stirrer and low temperature thermometer were added 100 gm of uridine intermediate from Example 2 and 1500 ml of tetrahydrofuran (THF) and the mixture was stirred for 5-10 min under nitrogen atmosphere at 25-30° C. 54.8 gm of MgCl$_2$ was added and the mixture was stirred for 2 hours. 261.0 gm of phosphoramide intermediate from Example 3 was slowly added and the mixture was stirred for 8-10 hrs at the same temperature. After completion of the reaction (as determined by HPLC), the THF was distilled out at below 45° C. and the reaction mass was allowed to cool at 25-30° C. 1.0 L dichloromethane and 1.0 L of aqueous ammonium chloride solution was added to the reaction mass, and the solution was stirred at room temperature to separate the layers.

The obtained organic layer was distilled out completely to obtain a residue, followed by addition of 300 mL of MDC (dichloromethane) and 300 mL MTBE. The reaction mixture was stirred for 6 hrs. at 25-30° C. and then cooled to 10-15° C. and stirred again for 2 hrs. The resultant precipitated material was filtered, washed with a mixture of dichloromethane and MTBE (1:1) and dried under vacuum for 15 min at 50-60° C. to isolate the title product. (Yield: 70-80%)

Example-5

Preparation of Sofosbuvir

To a 4 L of four-necked round bottom flask fitted with a mechanical stirrer and low temperature thermometer were added 100 gm of uridine intermediate from Example 2 and 1500 mL of tetrahydrofuran (THF) and the reaction mixture was stirred for 5-10 min under nitrogen atmosphere at 25-30° C. 54.8 gm of LiCl was added and the reaction mixture was stirred for 2 hours, followed by slow addition of 261.0 gm of phosphoramide intermediate from Example 3 and stirring for 8-10 hrs. at the same temperature. After completion of the reaction (as determined by HPLC), the THF was distilled out at below 45° C. and the reaction mass was allowed to cool at 25-30° C. 1.0 L dichloromethane and 1.0 L of aqueous ammonium chloride solution was added to the reaction mass, and the solution was stirred at room temperature to separate the layers.

The obtained organic layer was distilled out completely to obtain a residue, followed by addition of 300 mL of MDC and 300 mL MTBE. The reaction mixture was stirred for 6 hrs. at 25-30° C. and then cooled to 10-15° C. and stir for 2 hrs. The resultant precipitated material was filtered, washed with a mixture of dichloromethane and MTBE (1:1) and dried under vacuum for 15 min at 50-60° C. to isolate the title product. (Yield: 60-70%)

Throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

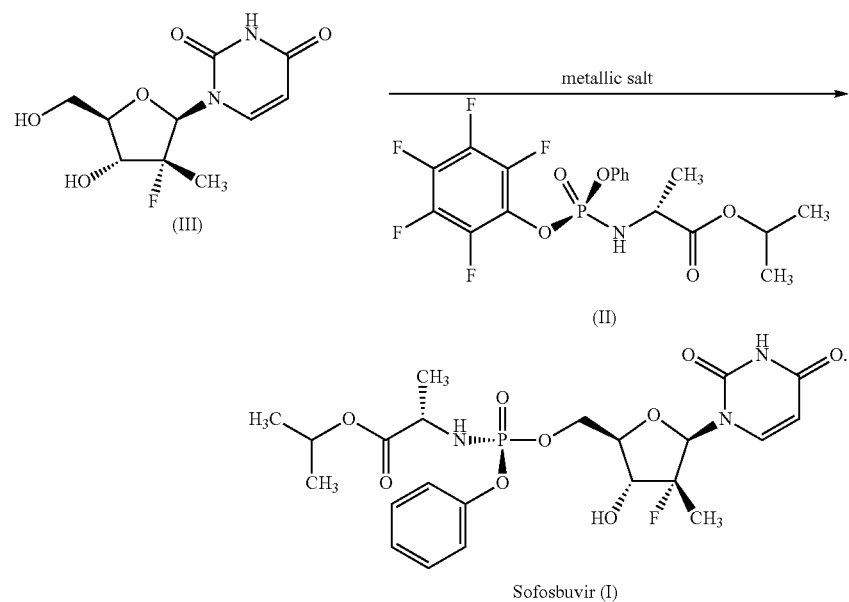

We claim:

1. A process for the preparation of sofosbuvir of formula (I) comprising the step of reacting a compound of formula (III), 2'-deoxy-2'-fluoro-2'-C-methyluridine, with a compound of formula (II), (S)-isopropyl-2-(((R)-[(2,3,4,5,6-pentafluoro-phenoxy-phosphorylamino]propanoate, in the presence of a metallic salt, optionally further in the presence of a base and a solvent, to obtain sofosbuvir of formula (I)

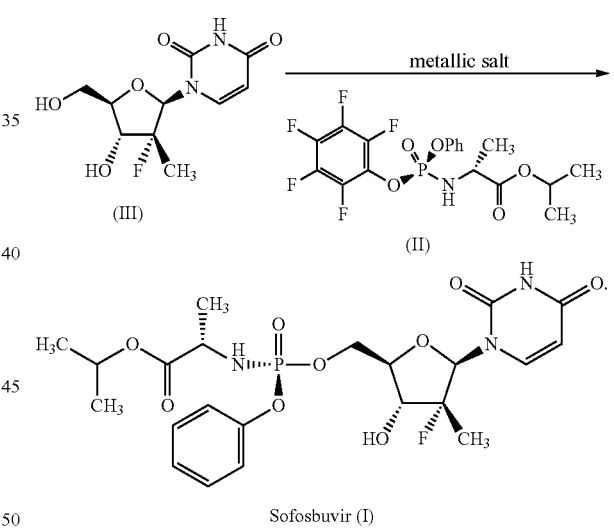

2. The process of claim 1, further comprising preparing the compound of formula (III) by:
(i) deprotecting a compound of formula (V) in an acid and a solvent to obtain a compound of formula (IV)

-continued

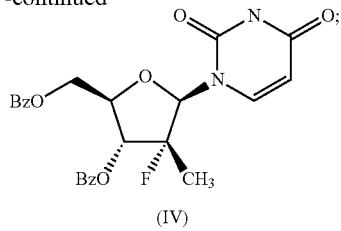

(IV)

and (ii) hydrolyzing the compound of formula (IV) in the presence of a base and a solvent to obtain a compound of formula (III)

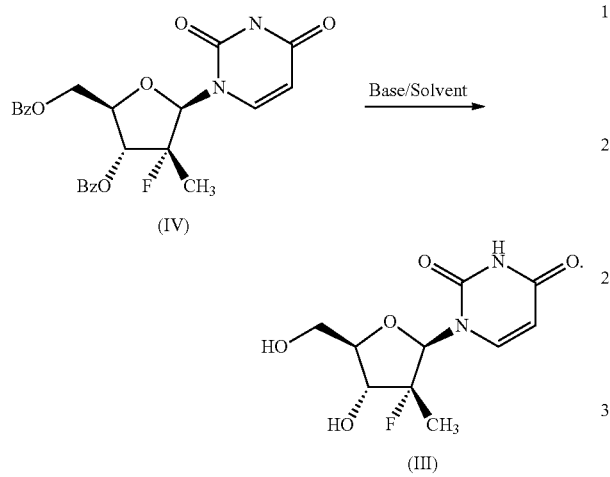

3. The process according to the claim 1, wherein the reaction is carried out in the presence of a solvent selected from acetone, tetrahydrofuran, acetonitrile, ethyl acetate, dimethylformamide, dichloromethane, methyl tertiary butyl ether, methanol, ethanol, isopropanol, water and mixtures thereof.

4. The process according to claim 3, wherein the solvent is selected from methanol, tetrahydrofuran, and mixtures thereof.

5. The process according to claim 3, wherein the solvent in is tetrahydrofuran.

6. The process according to claim 2, wherein the solvent in step (ii) is methanol.

7. A process according to claim 2, wherein the base in step (ii) is ammonia.

8. The process according to the claim 2, further comprising deprotecting the compound of formula (V) by reaction with a deprotection agent selected from trifluoroacetic acid, sulphuric acid, methane sulphonic acid, acetic acid, formic acid, hydrochloric acid, and mixtures thereof to form the compound of formula (IV).

9. The process according to claim 2, wherein the acid in step (i) is acetic acid.

10. The process according to claim 2, wherein the acid in step (i) is 80% acetic acid.

11. The process according to claim 1, wherein the reaction is carried out in the presence of a base selected from ammonium acetate, ammonium chloride, ammonium formate, ammonium sulfamate, ammonium phosphate, ammonium citrate, ammonium carbamate, ammonia, and mixtures thereof.

12. The process according to claim 1, wherein the reaction is carried out in the presence of a metallic salt selected from magnesium chloride, magnesium bromide, magnesium iodide, lithium chloride, lithium bromide, lithium iodide, copper chloride, copper bromide, copper iodide, and mixtures thereof.

13. The process according to claim 12, wherein the metallic salt is magnesium chloride.

14. The process according to claim 1, wherein the reaction is performed in the absence of a Grignard reagent.

15. The process according to claim 1, further comprising recrystallizing the compound of formula (I) in the presence of an ether solvent.

16. The process according to claim 15, wherein the ether solvent is selected from diethyl ether, diisopropyl ether, MTBE (methyl tertiary butyl ether), and mixtures thereof.

17. The process according to claim 16, wherein the ether solvent is MTBE.

18. A process for the preparation of sofosbuvir of formula (I) comprising the steps of
(a) deprotecting $N^4,3',5'$-tribenzoyl-2'-deoxy-2'-fluoro-2'-C-methylcytidine of formula (V) in the presence of an acid to obtain 3',5'-dibenzoyl-2'-deoxy-2'-fluoro-2'-C-methyluridine of formula (IV)

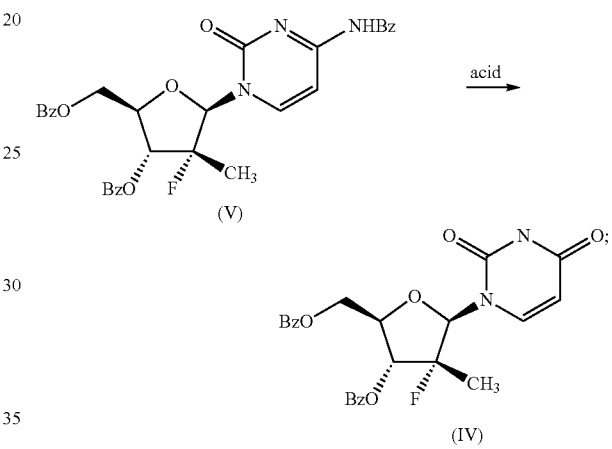

(b) hydrolyzing the 3',5'-dibenzoyl-2'-deoxy-2'-fluoro-2'-C-methyluridine of formula (IV) in the presence of a base and a solvent to obtain 2'-deoxy-2'-fluoro-2'-C-methyluridine of formula (III)

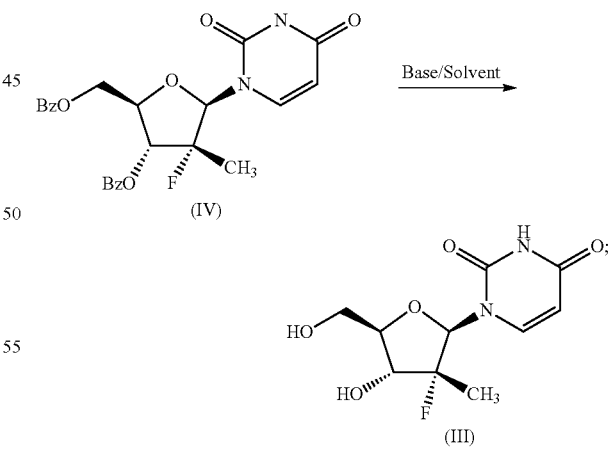

and (c) reacting the 2'-deoxy-2'-fluoro-2'-C-methyluridine of formula (III) with (S)-isopropyl-2-(((R)-[(2,3,4,5,6-pentafluoro-phenoxy-phosphorylamino]propanoate of formula (II) in the presence of a metallic salt, optionally further in the presence of a base and a solvent, to obtain sofosbuvir of formula (I)